(12) United States Patent
Johnson

(10) Patent No.: US 7,142,988 B1
(45) Date of Patent: Nov. 28, 2006

(54) METHOD AND INFORMATION SYSTEM FOR NON-RANDOM SELECTION OF UNIFORM STRUCTURAL AND FUNCTIONAL FEATURES FOR TISSUE AND PLANT PRODUCT PROCESSING

(75) Inventor: Peter C. Johnson, Wexford, PA (US)

(73) Assignee: Monsanto Company, St. Louis, MO (US)

( * ) Notice: Subject to any disclaimer, the term of this patent is extended or adjusted under 35 U.S.C. 154(b) by 0 days.

(21) Appl. No.: 09/521,769

(22) Filed: Mar. 9, 2000

Related U.S. Application Data

(60) Provisional application No. 60/152,661, filed on Sep. 7, 1999.

(51) Int. Cl.
 *G06F 19/00* (2006.01)
 *G01N 35/00* (2006.01)
(52) U.S. Cl. ............................................ 702/20; 702/40
(58) Field of Classification Search ................ 47/1.01; 702/19; 435/6; 424/773; 356/432, 456
See application file for complete search history.

(56) References Cited

U.S. PATENT DOCUMENTS

| | | | | |
|---|---|---|---|---|
| 4,437,934 A | | 3/1984 | Nelson et al. ............. | 159/47.1 |
| 5,130,545 A | * | 7/1992 | Lussier .................... | 250/458.1 |
| 5,370,713 A | * | 12/1994 | Hanseler | |
| 5,526,258 A | | 6/1996 | Bacus ..................... | 364/413.1 |
| 5,845,229 A | | 12/1998 | Rawlins ......................... | 702/2 |
| 6,100,030 A | | 8/2000 | McCasky Feazel et al. .... | 435/6 |
| 6,851,662 B1 | * | 2/2005 | Panigrahi et al. ........... | 356/326 |

FOREIGN PATENT DOCUMENTS

| | | |
|---|---|---|
| RU | 1839074 | 12/1993 |
| WO | WO 99/03557 | 1/1999 |

OTHER PUBLICATIONS

Chappelle et al. "Laser- induced fluorescence of green plants. 1: A technique for the remote detection of plant stress and species differentiation." Jan. 1984, Applied Optics, vol. 23 No. 1 134-138.*
Shibusawa et al., Discriminate method with image data to select the plant with superior characteristics from interspecific hybrids of *Discorea*-spp., Mem. Fac. Agric. Hokkaido Univ., 1990, vol. 17, No. 1, pp. 94-106 (with English summary).
Cazzulino et al., Rapid quantitative screening of somatic plant embryos by image analysis, Abstracts of the Chemical Congress of North America, 1988. vol. 3, No. 2, MBTD 31 Abstract only.
Michaels, T.E., A digital image analysis method for selecting ozone-insensitive white beans, Can. J. Plant. Sci. 1988. vol. 68, pp. 627-632.
Chtioui et al., Feature selection by a genetic algorithm. Application to seed discrimination by artificial vision, J. Sci. Food Agric., 1998 vol. 76, No. 1, pp. 77-86.
S.D. Tanksley et al., "Use of molecular markers in breeding for soluble solids content in tomato- a re-examination," Theoretical and Applied Genetics, Springer, Berlin, Germany, vol. 75, 1988, p. 811-823.
Database FSTA Online, International Food Information Service (IFIS), Frankfurt, Germany, Jan. 1, 1978, Pathak S.R. et al., "Evaluation of tomato (*Lycopersicon esculentum* Mill.) cultivars for processing," Indian Food Packer, 1978, vol. 32, p. 25-31.

* cited by examiner

*Primary Examiner*—Marjorie A. Moran
(74) *Attorney, Agent, or Firm*—Howrey LLP

(57) ABSTRACT

The present invention discloses a novel method and an information system for allowing a non-random selection of a genotype of a plant cultivar that yields a selected plant product with desired processing features. The method involves determining structural and functional variables of the selected plant product, genetic variables responsible for said structural and functional variables and processing variables of the selected plant, and correlating the structural and functional variables to the genetic variables and to the processing variables so as to make a non-random selection of the genotype of the plant cultivar that yields the plant product with desired processing features.

8 Claims, 14 Drawing Sheets

250a →     251a →

| GENETIC INFORMATION CULTIVAR 1 253a | GENETIC INFORMATION CULTIVAR 1 254a |
|---|---|
| • FRUIT SIZE GENE(S) $f_1 f_2 f_3 f_4$<br>• $\beta$-CAROTENE GENE(S) $B_1$<br>• LYCOPENE CONTENT GENE(S) $hp_1$<br>• FRUIT SUGAR GENE(S) $s_1$ | • FRUIT SIZE GENE(S) $f_1 f_2 f_3 f_4$<br>• $\beta$-CAROTENE GENE(S) $B_1$<br>• LYCOPENE CONTENT GENE(S) $hp_1$<br>• FRUIT SUGAR GENE(S) $s_1$ |
| GROWTH CONDITIONS INFORMATION SET 1 240a | GROWTH CONDITIONS INFORMATION SET 2 241a |
| • DAY TEMPERATURE 15-20°C<br>• SOIL FERTILITY 6000 (kg NITROGEN/HA)<br>• SOIL MOISTURE 20% | • DAY TEMPERATURE 23-25°C<br>• SOIL FERTILITY 4000 (kg NITROGEN/HA)<br>• SOIL MOISTURE 30% |
| PRODUCT FEATURE RANGE SET 1 256a | PRODUCT FEATURE RANGE SET 2 257a |
| • FRUIT SIZE 50-60mm<br>• $\beta$-CAROTENE 8-10ppm<br>• LYCOPENE 90-100ppm<br>• TOTAL FRUIT SUGARS 65-70% | • FRUIT SIZE 70-80mm<br>• $\beta$-CAROTENE 4-6ppm<br>• LYCOPENE 70-80ppm<br>• TOTAL FRUIT SUGARS 65-70% |

| GENETIC INFORMATION CULTIVAR 1 255a | GENETIC INFORMATION CULTIVAR 2 253b |
|---|---|
| • FRUIT SIZE GENE(S) $f_1 f_2 f_3 f_4$<br>• $\beta$-CAROTENE GENE(S) $B_1$<br>• LYCOPENE CONTENT GENE(S) $hp_1$<br>• FRUIT SUGAR GENE(S) $s_1$ | • FRUIT SIZE GENE(S) $f_1 f_2$<br>• $\beta$-CAROTENE GENE(S) $B_1 B_2$<br>• LYCOPENE CONTENT GENE(S) $hp_1 hp_2$<br>• FRUIT SUGAR GENE(S) $s_1 s_2$ |
| GROWTH CONDITIONS INFORMATION SET 3 242a | GROWTH CONDITIONS INFORMATION SET 1 240b |
| • DAY TEMPERATURE 27-30°C<br>• SOIL FERTILITY 2000 (kg NITROGEN/HA)<br>• SOIL MOISTURE 50% | • DAY TEMPERATURE 15-20°C<br>• SOIL FERTILITY 6000 (kg NITROGEN/HA)<br>• SOIL MOISTURE 20% |
| PRODUCT FEATURE RANGE SET 1 258a | PRODUCT FEATURE RANGE SET 1 256b |
| • FRUIT SIZE 90-100mm<br>• $\beta$-CAROTENE 1-2ppm<br>• LYCOPENE 55-65ppm<br>• TOTAL FRUIT SUGARS 65-70% | • FRUIT SIZE 55-60mm<br>• $\beta$-CAROTENE 9-10ppm<br>• LYCOPENE 95-100ppm<br>• TOTAL FRUIT SUGARS 65-70% |

FROM FIG. 3A            TO FIG. 3C

| GENETIC INFORMATION CULTIVAR 2 254b | GENETIC INFORMATION CULTIVAR 2 255b |
|---|---|
| • FRUIT SIZE GENE(S) $f_1 f_2$<br>• $\beta$-CAROTENE GENE(S) $B_1 B_2$<br>• LYCOPENE CONTENT GENE(S) $hp_1 hp_2$<br>• FRUIT SUGAR GENE(S) $s_1 s_2$ | • FRUIT SIZE GENE(S) $f_1 f_2$<br>• $\beta$-CAROTENE GENE(S) $B_1 B_2$<br>• LYCOPENE CONTENT GENE(S) $hp_1 hp_2$<br>• FRUIT SUGAR GENE(S) $s_1 s_2$ |
| GROWTH CONDITIONS INFORMATION SET 2 241b | GROWTH CONDITIONS INFORMATION SET 3 242b |
| • DAY TEMPERATURE 23-25°C<br>• SOIL FERTILITY 4000 (kg NITROGEN/HA)<br>• SOIL MOISTURE 30% | • DAY TEMPERATURE 27-30°C<br>• SOIL FERTILITY 2000 (kg NITROGEN/HA)<br>• SOIL MOISTURE 50% |
| PRODUCT FEATURE RANGE SET 2 257b | PRODUCT FEATURE RANGE SET 1 258b |
| • FRUIT SIZE 75-80mm<br>• $\beta$-CAROTENE 5-6ppm<br>• LYCOPENE 75-80ppm<br>• TOTAL FRUIT SUGARS 65-70% | • FRUIT SIZE 20-30mm<br>• $\beta$-CAROTENE 0.1-0.3ppm<br>• LYCOPENE 20-25ppm<br>• TOTAL FRUIT SUGARS 65-70% |

FROM FIG. 3B         TO FIG. 3D

| GENETIC INFORMATION CULTIVAR X 253x | GENETIC INFORMATION CULTIVAR X 254x |
|---|---|
| • FRUIT SIZE GENE(S) $f_1$<br>• $\beta$-CAROTENE GENE(S) $B_1B_2B_3B_4$<br>• LYCOPENE CONTENT GENE(S) $hp_1hp_2hp_3hp_4$<br>• FRUIT SUGAR GENE(S) $S_1S_2S_3S_4$ | • FRUIT SIZE GENE(S) $f_1$<br>• $\beta$-CAROTENE GENE(S) $B_1B_2B_3B_4$<br>• LYCOPENE CONTENT GENE(S) $hp_1hp_2hp_3hp_4$<br>• FRUIT SUGAR GENE(S) $S_1S_2S_3S_4$ |
| GROWTH CONDITIONS INFORMATION SET 1 240x | GROWTH CONDITIONS INFORMATION SET 2 241x |
| • DAY TEMPERATURE 5-20°C<br>• SOIL FERTILITY 6000 (kg NITROGEN/HA)<br>• SOIL MOISTURE 20% | • DAY TEMPERATURE 23-25°C<br>• SOIL FERTILITY 4000 (kg NITROGEN/HA)<br>• SOIL MOISTURE 30% |
| PRODUCT FEATURE RANGE SET 1 256x | PRODUCT FEATURE RANGE SET 2 257x |
| • FRUIT SIZE 50-60mm<br>• $\beta$-CAROTENE 6-8ppm<br>• LYCOPENE 75-85ppm<br>• TOTAL FRUIT SUGARS 50-55% | • FRUIT SIZE 70-80mm<br>• $\beta$-CAROTENE 1-2ppm<br>• LYCOPENE 55-65ppm<br>• TOTAL FRUIT SUGARS 55-65% |

FROM FIG. 3C          TO FIG. 3E

GENETIC INFORMATION CULTIVAR X 255X

- FRUIT SIZE GENE(S) $f_1$
- $\beta$-CAROTENE GENE(S) $B_1B_2B_3B_4$
- LYCOPENE CONTENT GENE(S) $hp_1hp_2hp_3hp_4$
- FRUIT SUGAR GENE(S) $S_1S_2S_3S_4$

GROWTH CONDITIONS INFORMATION SET 3 242X

- DAY TEMPERATURE 27-30°C
- SOIL FERTILITY 2000 (kg NITROGEN/HA)
- SOIL MOISTURE 50%

PRODUCT FEATURE RANGE SET 3 258X

- FRUIT SIZE 90-100mm
- $\beta$-CAROTENE 1-2ppm
- LYCOPENE 55-65ppm
- TOTAL FRUIT SUGARS 65-70%

FROM FIG. 3D

PRODUCT PROCESSING DATA SET 1 352a
- MILLING TIME 15 MIN.
- HEATING TEMP 90°C
- ...
- ...

PRODUCT PROCESSING FEATURE RANGE SET 1 354a
- LYCOPENE 55-65 ppm
- SIZE 90-100 mm
- TOTAL FRUIT SUGARS 65-70%
- β-CAROTENE CONTENT 1-2 ppm
- ...
- ...

350b

PRODUCT PROCESSING DATA SET 2 352b
- MILLING TIME 10 MIN.
- HEATING TEMP 80°C
- ...
- ...

PRODUCT PROCESSING FEATURE RANGE SET 2 354b
- LYCOPENE 70-80 ppm
- SIZE 70-80 mm
- TOTAL FRUIT SUGARS 65-70%
- β-CAROTENE CONTENT 4-6 ppm
- ...
- ...

350x

PRODUCT PROCESSING DATA SET n 352x
- MILLING TIME 5 MIN.
- HEATING TEMP 70°C
- ...
- ...

PRODUCT PROCESSING FEATURE RANGE SET n 354x
- LYCOPENE 90-100 ppm
- SIZE 50-60 mm
- TOTAL FRUIT SUGARS 65-70%
- β-CAROTENE CONTENT 8-10 ppm
- ...
- ...

FIG. 6

METHOD AND INFORMATION SYSTEM FOR NON-RANDOM SELECTION OF UNIFORM STRUCTURAL AND FUNCTIONAL FEATURES FOR TISSUE AND PLANT PRODUCT PROCESSING

This application claims the priority of U.S. Provisional Application No. 60/152,661 filed Sep. 7, 1999.

FIELD OF THE INVENTION

This application relates to a method and an information system for predicting structural and processing features of a selected plant, plant product or living tissue. More particularly, it concerns a non-random prediction of microscopic structure, function and processing features of selected crop cultivars.

BACKGROUND OF THE INVENTION

Crop plants that are commercially grown today for various products such as seed, fruit, fiber and vegetables are developed by breeders through vigorous breeding programs. The breeder initially selects and crosses two or more parental lines, followed by repeated selfing and selection producing many new genetic combinations. The breeder can generate billions of different genetic combinations via crossing, selfing and mutations. The breeder has no direct control at the tissue or cellular level. A breeder of ordinary skill in the art cannot predict the products resulting from the cultivars he or she develops, except possibly in a random and a very general fashion. To put it in another way, the same breeder cannot produce the same cultivar twice by using the exact same original parents and the same selection techniques. Particularly, in the breeding of cross-pollinated species, each generation brings a reshuffling and regrouping of the genes. The resulting cultivars or varieties vary too much for accurate labeling. Therefore, the cultivars which are developed are unpredictable. This unpredictability is because breeder's selection occurs in unique environments with millions of different possible genetic combinations being generated within the gene pool, and with no direct control at the microscopic structural features at the cellular level and the nucleic acid level or the processing features. Therefore, even a carefully selected variety produces raw materials with non-uniform properties. Structural features of a product have direct bearing upon the product processing. For example, the energy required to peel or slice, dice or macerate a fruit or vegetable is functionally related to the microstructural components of the plant including cell wall density and thickness.

The Food and Drug Administration has mandated standard labeling for all processed food. This requires manufacturers to use uniform quality products and clearly label their product with the caloric, fat, protein and vitamin contents as a percent of the daily values of an adult 2000 calorie diet. The presently available cultivars although generally uniform, vary too much to label accurately.

For example, one of the difficulties with tomato products and food industry that uses tomato products is to produce products of constant quality, for example, products of constant color or constant shape. The shape of the tomato differs from one variety of tomato to another and changes in different seasons, depends on agronomic conditions, weather and location. At the same time, the presently available tomato processing systems are designed to process the best quality products, such as the most perfectly shaped tomatoes or canned whole peeled tomatoes, or red pigment of the tomato. These products must look perfect to the consumer and consequently the percentage of rejects in the various operations is very high and influences processing costs and the cost of the final product.

For food retailers such as grocery stores, the variability in size alone adds millions of dollars to the annual handling costs of produce. Fast food restaurants also spend thousands of dollars per day sorting different vegetables such as potatoes, cucumbers, tomatoes and lettuce to assure the uniform quality of their salads. Similarly, one of the difficulties of seed industry is to produce seed of constant quality. Plant seeds of essentially all varieties are often processed by one or more procedures (e.g., grading) to classify and/or reject the seed according to the grading requirements to improve their quality and utility for a variety of uses such as planting, oil-extraction, storage, and subsequent processing for the manufacture of seed-derived products such as animal foods.

Thus, the inability to predict the desired processing quality reduces the economic returns and influences the processing costs.

The genetic information in a cell directs cellular function and determines cellular phenotype in a given environment. Due to the advent of technology, a comprehensive genetic information of all expressed genes has become a realized goal by genomics approaches. Comprehensive genetic maps are being constructed for all the genes of crop plants. Indeed, agriculture is now well positioned to take its share of the benefits of genomics. The study of plant morphology, anatomy physiology, metabolism, genetic engineering, agronomy and biochemistry has also led to important insights into various biological processes and agriculture. It is now virtually routine to introduce almost any gene or set of genes into many crop species. Control of endogenous gene expression is now possible in plants through the phenomenon of cosuppression.

What is needed is that all of the rich knowledge from the above studies need to be integrated and correlated to cell and tissue structure and content, so as to predict structural features of a selected variety in a non-random fashion.

From the foregoing, it is evident that a process and an information system having the elements necessary to enable the reasoned selection of a raw plant product of a selected plant and/or the non-random selection of a crop plant that yields a selected raw plant product with uniform features is desired such that the selected product can be processed into a uniform quality end product.

SUMMARY OF THE INVENTION

The method and information system of the invention allows a non-random selection of a raw plant product of a selected plant (which includes both wild and cultivated plants) and/or the non-random selection of a crop plant that yields a selected raw plant product with uniform features such that the selected product can be processed into a uniform quality end product. In general aspects of the invention, the method involves, as step (a), obtaining of a sample of the raw product of the selected plant. Then the method involves, as step (b), analyses of the sample to determine one or more structural or functional indices associated with the raw product. The structural or functional indices include plant phenomic indices which can be macrophenomics or microphenomics indices. Further, the structural or functional indices include qualitative features and/or a quantitative features.

The selected raw plant product that is obtained for analysis can be a group fruits, a group of tubers, a group of seeds, a group of leaves, a group of vegetative buds, a group of inflorescences, a group of nuts or a group of seeds. The selected plant product is analyzed by means of an imaging system such as a light microscope, fluorescent microscope, spectral microscope, hyper-spectral microscope, electron microscope, confocal microscope optical coherence tomograph telescope, spectral telescope, MRI and/or ultrasound, and such other techniques to determine one or more structural or functional indices associated with the raw product.

Specifically, in one aspect of the invention the method involves, in addition to the steps mentioned in the general aspects of the invention, the steps of: (c) providing a plurality of product processing feature range set records, where each of the records associates a given set of product processing data with a corresponding product processing feature range set, and where for each such record, a uniform quality end product results from application of the given set of product processing data to raw product falling within the associated product processing feature range set; (d) determining the suitability of the sample obtained in step (a) for processing into the uniform quality end product by comparing the at least one structural or functional index to product processing feature range sets in the records; and (e) if the at least one structural or functional index matches one of the product processing feature range sets in the records then, selecting the raw product so that when processed under a given set of processing parameters, the selected raw product results in the uniform quality end product. The processing parameters include bioprocessing data.

In another aspect of the invention, a method for non-random selection of a crop plant that yields a selected raw plant product with uniform features for processing into a uniform quality end product is provided which includes, in addition to the steps mentioned in the general aspects of the invention, the following steps: (c) providing a plurality of product processing feature range set records, wherein each of the records associates a given set of product processing data with a corresponding product processing feature range set, and wherein, for each such record, a uniform quality end product results from application of the given set of product processing data to raw product falling within the associated product processing feature range set; (d) determining the suitability of the sample for processing into the uniform quality end product by comparing the at least one structural or functional index to each product processing feature range set in the records; and (e) if the at least one structural or functional index matches one of the product processing feature range sets in the records then, selecting the crop plant for growing under a selected set of growth conditions whereby the selected crop plant yields raw product suitable for processing into the uniform quality end product.

In still another aspect of the invention, a method for non-random selection of a crop plant that yields a selected raw plant product with uniform features for processing into a uniform quality end product is provided which includes, in addition to the steps mentioned in the general aspects of the invention, the following steps: (c) providing a plurality of product feature range set records, where each of the product feature range set records associates a given set of genetic information of a cultivar of the crop plant with a corresponding product feature range set and with a corresponding set of growth conditions suitable for growing the cultivar to produce the selected raw plant product with indices that fall within the associated product feature range set; (d) identifying a first cultivar by comparing the at least one structural or functional index analyzed in step (b) to each of the records in step (c); (e) providing a plurality of product processing feature range set records, wherein each of the product processing feature range set records associates a given set of product processing data with a corresponding product processing feature range set, and wherein, for each such record, a uniform quality end product results from application of the given set of product processing data to raw product falling within the associated product processing feature range set; (f) determining the suitability of the sample for processing into the uniform quality end product by comparing the at least one structural or functional index to each product processing feature range set in the records; (g) if the at least one structural or functional index matches one of the product processing feature range sets in the records then, selecting the first cultivar and recommending the first cultivar for growing under the given set of growth conditions. In this aspect, the method can include the following further steps: (h) if the at least one structural or functional index does not match one of the product processing feature range sets in the records then, searching one or more classes of genome databases for one or more genes that code for the desired product features deficient in the first cultivar and recommending genetic engineering of the first cultivar to introduce said genes into the first cultivar so as to produce a modified cultivar, which modified cultivar produces the selected raw plant product with the at least one structural or functional index that matches one of the records in step (f), or selecting a second cultivar that produces the selected raw plant product with the at least one structural or functional index having the closest match to one of the records in step (f) and reiterating the necessary steps until the at least one structural or functional index matches one of the product processing feature range sets in the records. The selection of one or more genes from one or more classes of genomic databases can be done by providing a processing control system for this purpose.

In yet another aspect of the invention, a method for non-random selection of a crop plant that yields a selected raw plant product with uniform features for processing into a uniform quality end product is provided which includes, in addition to the steps mentioned in the general aspects of the invention, the following steps: (c) providing a plurality of product feature range set records, where each of the product feature range set records associates a given set of genetic information of a cultivar of the crop plant with a corresponding product feature range set and with a corresponding set of growth conditions suitable for growing the cultivar to produce the selected raw plant product with indices that fall within the associated product feature range set; (d) identifying a first cultivar by comparing the at least one structural or functional index analyzed in step (b) to each of the records in step (c); (e) providing a plurality of product processing feature range set records, wherein each of the product processing feature range set records associates a given set of product processing data with a corresponding product processing feature range set, and wherein, for each such record, a uniform quality end product results from application of the given set of product processing data to raw product falling within the associated product processing feature range set; (f) determining the suitability of the sample for processing into the uniform quality end product by comparing the at least one structural or functional index to each product processing feature range set in the records; (g) if the at least one structural or functional index matches one of the product processing feature range sets in the records then, selecting the first cultivar and recommending the first cultivar for growing under the given set of growth conditions; (h) if the at least one structural or functional index does not match one of the product processing feature range sets in the records then, searching one or more classes of genome databases for one or more genes that code for the desired product features deficient in the first cultivar and recommending genetic engineering of the first cultivar to introduce said genes into the first cultivar so as to produce a modified cultivar, which modified cultivar produces the selected raw plant product with the at least one structural or functional index that matches one of the records in step (f), or selecting a second cultivar that produces the selected raw plant product with the at least one structural or functional index having the closest match to one of the records in step (f), and reiterating the necessary steps until the at least one structural or functional index matches one of the product processing feature range sets in the records.

In another aspect of the present invention, a method for non-random selection of a sample of a tissue or a living tissue (such as a tissue from a fish, oyster, squid etc.) of an organism for processing into a uniform quality end product. The method involves the steps of: (a) analyzing the sample to determine at least one structural or functional index associated with the living tissue; (b) providing a plurality of product processing feature range set records, wherein each of the records associates a given set of product processing data with a corresponding product processing feature range set, and wherein, for each such record, a uniform quality end product results from application of the given set of product processing data to raw product falling within the associated product processing feature range set; (c) determining the suitability of the living tissue for processing into the uniform quality end product by comparing the at least one structural or functional index to product processing feature range sets in the records; and (d) if the at least one structural or functional index matches one of the product processing feature range sets in the records then, selecting the living tissue so that when processed the selected living tissue results in the uniform quality end product.

In the present invention, an information system for making non-random selection of a of crop plant that yields a selected raw plant product with uniform features for processing into a uniform quality end product is also provided. The information system has (a) an analyzing system for analyzing the selected plant product for obtaining information on at least one structural or functional index of the selected raw plant product; (b) a first database that stores information on the at least one structural or functional index analyzed by the analyzing system; (c) a second database that provides information on the plant genetic variables (genomic information), product features coded for by the genetic variables under a given set of growth conditions; and (d) a third database that provides processing information to determine processing variables for the structural and functional variables, where the first database is linked to the second database to compare the at least one structural or functional index in the first database with said information in the second database and to the third database to compare the at least one structural or functional index to said processing variables such that the information system facilitates the non-random selection of the crop plant that yields the selected plant product. The information system may further have a processing control system which is linked to the second database to determine specific genetic variables lacking in the second database to produce a plant product having specific structural and functional features and to the third database. The process control system is also linked to all genomic databases to identify if the needed genetic variables are available in any of those genomic databases. The growth conditions information can either be included in the second database or the information system can further include a fourth database that provides information on growth conditions (environmental conditions) to determine environmental variables responsible for the structural and functional variables. The information system can still further include a fifth database that provides agronomic information from an area of interest to enable crop management decisions. The information system can also have a GIS and/or GPS database to enable site-specific farming decisions.

In still another aspect of the present invention an information system useful for making a non-random selection of a desired genotype of a plant cultivar that yields a selected plant product having desired processing features is provided. The information system has the following elements: (a) a system for analyzing the selected plant product for obtaining information on phenomics to determine structural and functional variables of the selected plant product; (b) a first database that stores information on the structural and functional variables of the selected plant product; (c) a second database that provides information on the plant genomics to determine genetic variables responsible for each of the structural and functional variables; and (d) a third database that provides processing information to determine processing variables for the structural and functional variables, where the first database is linked to the second database to correlate the structural and functional variables to the genetic variables and to the third database to correlate the structural and functional variables to the processing variables such that the information system facilitates the non-random selection of the desired genotype that yields the selected plant product.

BRIEF DESCRIPTION OF THE DRAWINGS

The features, objects and advantages of the present invention will become further apparent from the description that follows when taken in conjunction with the following drawings.

FIGS. 3A, 3B, and 3C are diagrams showing a database for storing genetic variables of different cultivars and product features encoded by the genetic variables under different growth conditions. FIG. 3A is Cultivar 1, FIG. 3B is Cultivar 2, and FIG. 3C is Cultivar X.

FIGS. 6A, 6B, and 6C are diagrams showing a database used for correlating measured indices from a sample with product processing data. FIG. 6A is Product Processing Set 1, FIG. 6B is Product Processing Set 2, and FIG. 6C is Product Processing Set N.

DETAILED DESCRIPTION OF THE INVENTION

The present invention provides a computer based comprehensive information system and a method which effectively enables one to automatically make reasoned selections of plant cultivars or any living tissue. For example, fruits and vegetables harvested in a field do not often fall into a single selected quality for processing. Therefore, for example, USDA provides official U.S. quality standards and grades for fresh fruits and vegetables for processing. The invention disclosed here provides a method and an information system to make reasoned selections of plant varieties or cultivars of a crop plant so that a non-random prediction of microscopic structure and processing features are made before the crop is sown in the field. A crop plant (e.g., tomato) can have a number of varieties or cultivars. A variety is a group of similar plants, which by structural features and performance can be identified from other varieties within the same species. The term's varieties and cultivars as used herein are interchangeable.

While the application of the information system and the method of the present invention are not limited, the present invention finds particular application with crop plants for the successful production of agricultural products with desired processing features with a final and ultimate benefit to an end use consumer. As will become apparent, the present invention can be utilized for solanaceous crop plants such as potatoes, tomatoes, peppers and related species; grain crops such as wheat, barley, rice rye and related species; maize, pearl millet, sorghum; legume crops such as alfalfa, beans (*phaseolus* and *vigna*) cool season food legumes, soybean; Brassicaceae crop plants such as cabbages, cauliflower, radish and oilseed rape; cotton and fruit species such as cranberries, blueberries, apples and pears.

On one hand, the method and information system of the invention should be able to facilitate selection of naturally occurring varieties with predictable processing features. On the other hand, the method and information system of the invention should be able to facilitate selection of varieties with predictable processing features after molecular and/or genetic manipulation approach is applied.

Figure 1A:
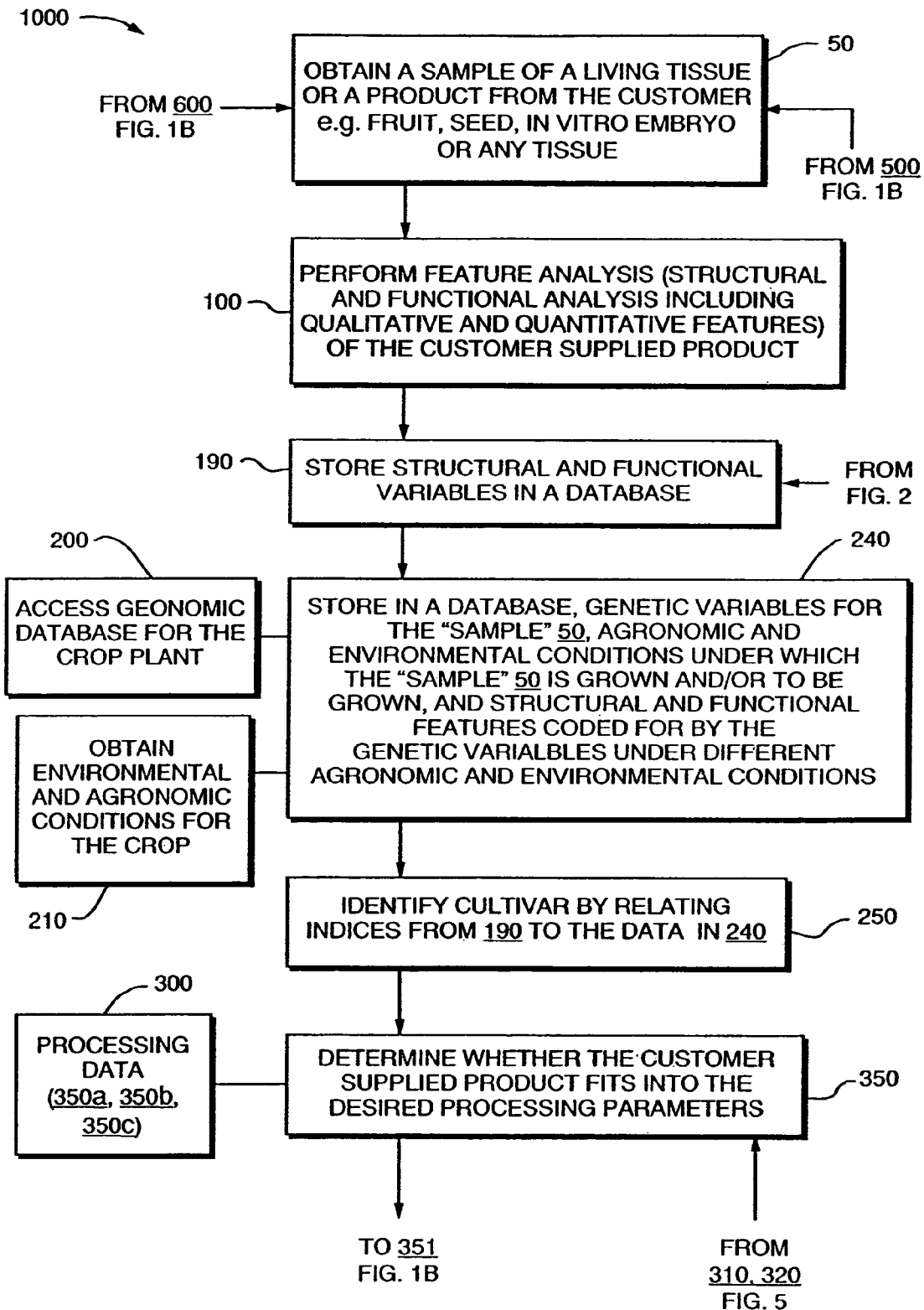
FIG. 1 is a flow diagram of a method for allowing non-random selection of a plant cultivar that produces a plant product with desired or required processing features.
Figure 1B:
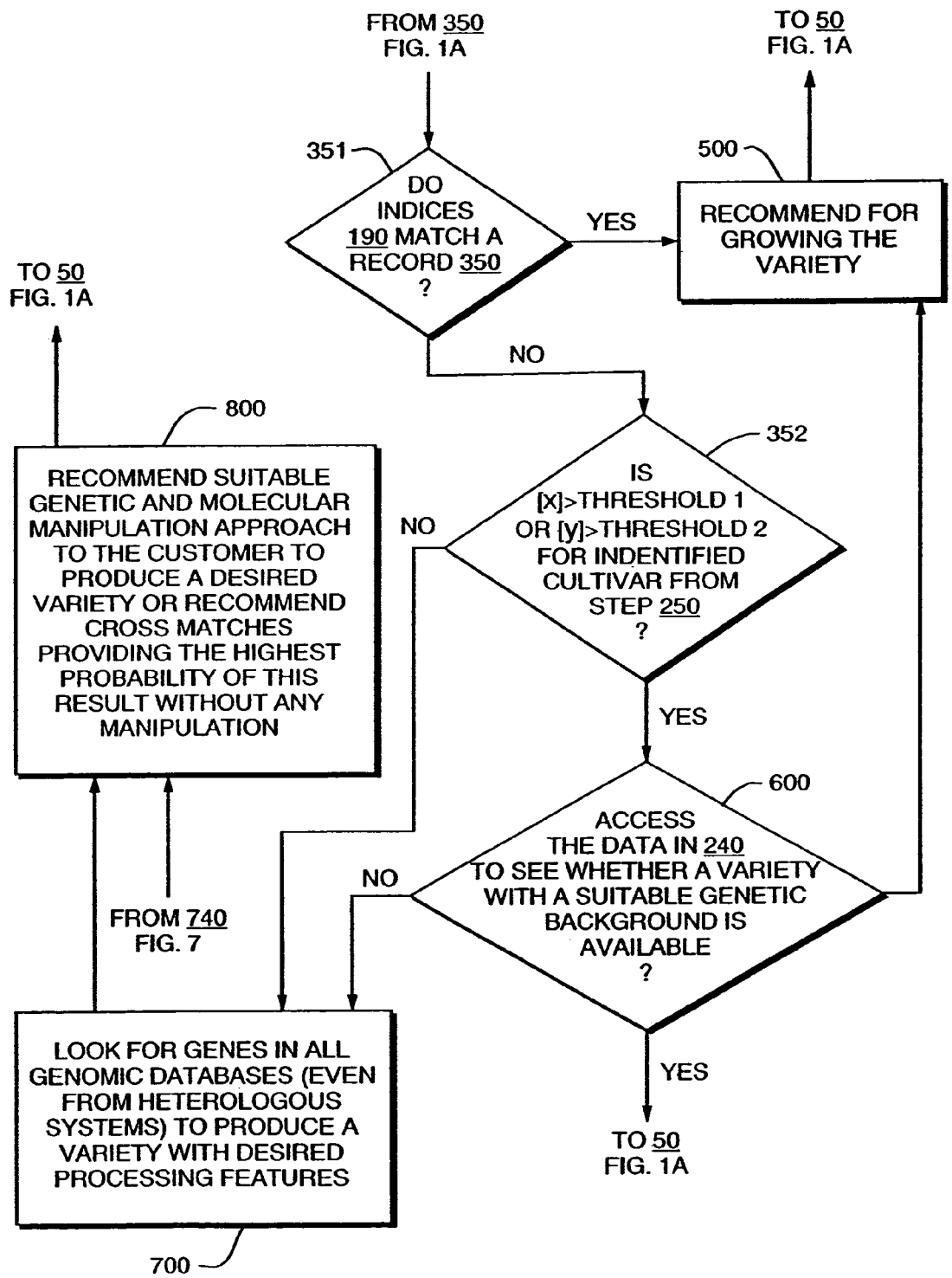

With reference to FIG. 1, a flow diagram of a method generally designated by reference numeral 1000 is shown. In step 50, a sample of a living tissue or a plant product is obtained from the customer for analysis, e.g., living tissue or a plant product including fruit tuber, seed or in vitro tissues such as embryos. In the example that will be used to illustrate the invention, the sample obtained in step 50 corresponds to a group of tomatoes of a given variety that have been grown in a given geographic area under a given set of environmental conditions. The number of tomatoes in the group (or sample) are sufficient to ensure that the results of the feature analysis (discussed below) correspond to statistically significant representations of the population of all tomatoes in the given variety that were grown in the given geographic area under the given set of environmental conditions. According to one aspect of the invention, the plant products (raw materials) so produced by the growers should have predictable processing variables (processing features) required processing the raw materials to the final product. It will be understood that in alternate embodiments, the sample provided in step 50 could include a group of seeds of a given variety, a group of in vitro tissue products such as plant embryos of the same variety, a group of living tissue specimens having common characteristics, a group of leaf tissue (or leaves) used as a salad or fodder, a group of inflorescence tissue (e.g., broccoli), a group of vegetable buds (e.g., cabbages, Brussels sprouts), a group of in vitro or field grown plant tubers of the same variety, or a group of any edible fruits of the same variety, etc. The variety associated with any given sample of fruit or seed can be a transgenic variety, a non-transgenic variety, or any genetically modified variety. Alternatively, in step 50 plant products of a given species naturally occurring in the wild can also be used. Referring again to the illustrative example of tomato fruit, in a particularly preferred embodiment, a sample of plant seed used to grow the given variety is also obtained in step 50.

A structural analysis on the sample obtained in step 50 is made in step 100. More particularly, in this step, a set of structural, mechanical and cell function indices for the sample are determined, for example, using the methods disclosed in U.S. patent application Ser. No. 09/338,904 entitled "Methods for Profiling and Manufacturing Tissue Using a Database that Includes Indices Representative of a Tissue Population", filed Jun. 23, 1999. In addition, in step 100, the following microscopic and macroscopic indices are determined for the sample: color, weight, size, shape, skin thickness, pulp density, pigment content, oil deposits, protein content, enzyme activity, lipid content, sugar and starch content, chlorophyll content, minerals, salt content, pungency, aroma and flavor and such other features. For each of these indices, a distribution of parameters is determined for the sample by determining a feature (e.g., weight) associated with each item in the sample, and then measuring mean and standard deviation values from the distribution. Macroscopic features, those that are readily apparent to the naked eye or by simple measurement, are referred herein as macrophenomics. Microscopic features are referred herein as microphenomics. The genomic expression of the plants led to recognizable macroscopic features. Similarly, the genomic expression of the plant leads to reproducible microscopic quantitative features as well.

Figure 2:
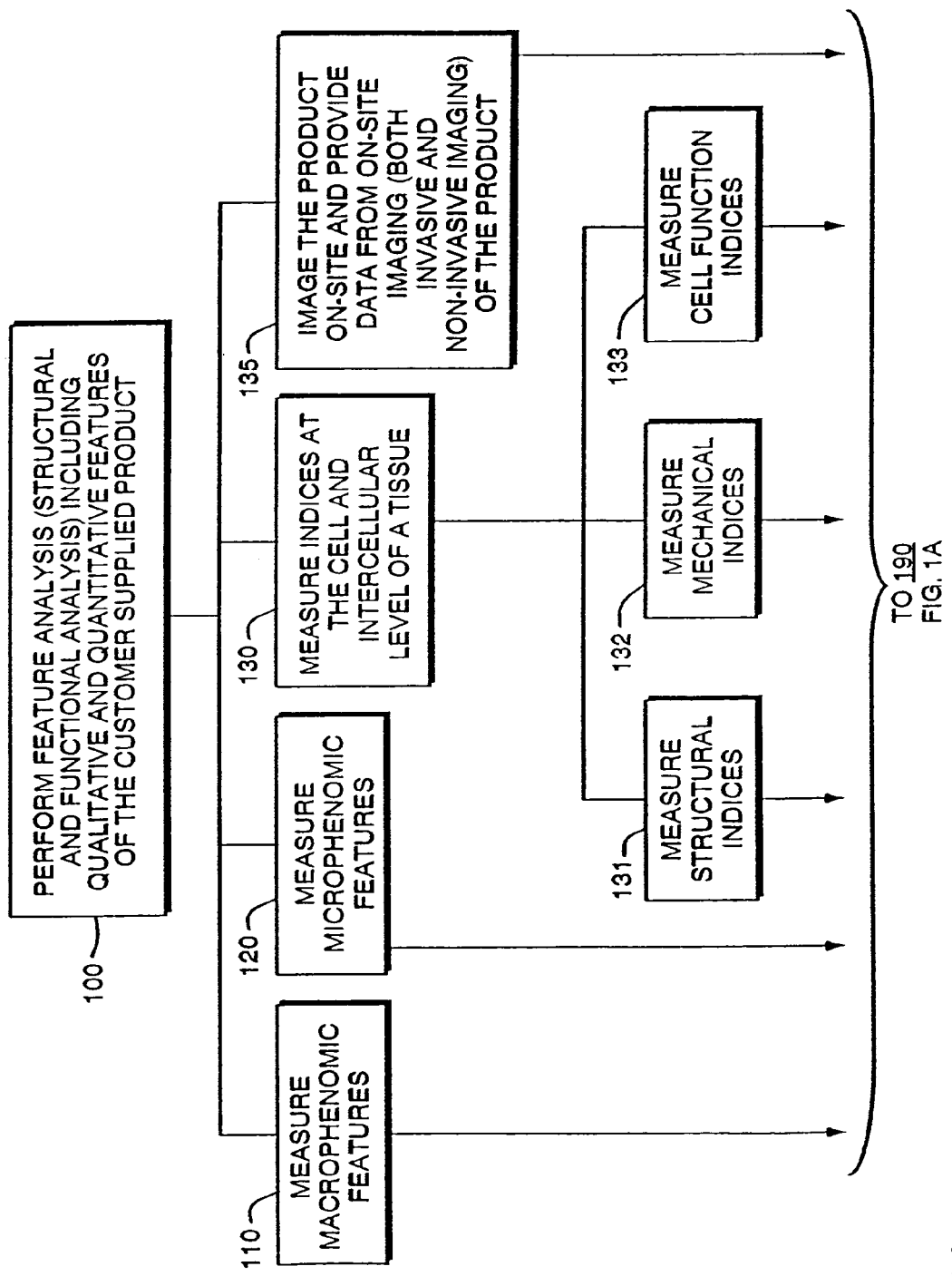
FIG. 2 is a flow diagram of a method for obtaining information on structural and functional features of the selected plant product.

A number of structural indices, mechanical indices and cell function indices have been disclosed in patent application Ser. No. 09/338,904. Such structural, mechanical and cell function indices as they are relevant to plants can be measured as part of the feature analysis in step 100. Thus in step 100, macrophenomic indices 110, microphenomic indices 120, and indices at the cell and intercellular level of a tissue 130 such as structural indices 131, mechanical indices 132 and cell function indices 133, collectively referred to herein as phenomics or phenomic indices or structural and functional variables, are determined. See, e.g., FIG. 2. Data from on-site imaging (invasive and/or non-invasive imaging) may be used to determine some of the indices described above.

The feature analysis at step 100 can be carried out using a variety of instruments and techniques. Preferably, various imaging modalities can be used for feature analysis as disclosed in patent application Ser. No. 09/338,904. For example, light microscopy, fluorescent microscopy, spectral microscopy, hyper-spectral microscopy, electron microscopy, confocal microscopy, optical coherence tomography, x-ray spectrometry, microtomy, in situ, NMR, ICP, ICP-Mass spectrometry and scanning fluorimetry can be used either singly or in combinations for feature analysis in accordance with the present invention.

For each of the indices 110, 120, 130, 131, 132 and 133, a sufficient number of measurements of the sample is taken to permit a statistically significant analysis that is representative of the given variety as a whole (i.e., a given variety that has been grown in a given geographic area under a given set of environmental conditions). To satisfy statistically significant representations, a randomly selected sample of the population is examined, randomness being important to ensure independence, which eliminates bias in selection of the sample. The sample size is large enough to represent faithfully the range of variability in the population for the feature under study. For example, the following description is provided to show how the statistically significant values are calculated from a sample data set. The data set can contain 100 observations or measurements made on a particular feature or character (e.g. fruit size) from a sample of 10 fruits obtained from different plants of a cultivar. The data can be arrayed from low to high for the observed values x, the frequency f of each observed value is noted, and the product fx are obtained. From the sum $\Sigma$ of its products fx the sample mean x is calculated. The range is the distance on the scale of measurements from the lowest to the highest observed value. From this data, the variance, the standard deviation and standard error can be calculated. A thorough description can be found in basic textbooks on statistics such as, for example, Dixon, W. J. et al., Introduction to Statistical Analysis, New York, McGraw-Hill (1969) or Steel R. G. D. et al., Principles and Procedures of Statistics: with Special Reference to the Biological Sciences, New York, McGraw-Hill (1960). There are also number of software programs for statistical analysis that are known to one skilled in the art. Thus structural and functional indices determined in step 100 should reflect a statistically significant number of samples for each product type. In step 190, indices 110, 120, 130, 131, 132 and 133 are stored in a database.

In step 200, a genomic database is accessed to retrieve genomic information (or genetic variables) of the selected crop plant (i.e., the given variety of tomato in the illustrative example). Plant genomics can be defined as the complete set of genetic instructions available for the plant gene expression that account for the structural and functional features of the plant. It should be noted that plant genomic information can be structural genomics information and/or functional genomic information. Structural genomics can include, but not be limited to, information from genotyping studies (where the inheritance of particular traits is studied using differences in the DNA sequence between dissimilar or different varieties of organisms), gene mapping studies (where after a gene of interest is localized to a particular region of the genome, an estimated map of the gene is constructed using overlapping or contiguous fragments of cloned DNA) and DNA sequencing studies.

Functional genomics can be defined as the correlation of expression patterns of gene sequences with structural and functional features that can be predicted on the basis of the gene expression. Functional genomics studies essentially involves constructing and characterizing a library of expressed gene sequences, and conducting large scale gene expression analysis to study gene function. Functional plant genomics and tools and systems to study functional plant genomics are well known to those skilled in the art. For example, some of the tools and systems that are well known include microarray gene expression profiling, computational biology, protein interaction analysis, model genetic organisms, plant-cell culture, transformation and gene expression analysis, and chemical annotation (e.g., dissection of biochemical pathways using directed agrochemical libraries for known target families of proteins). Thus, in step 200, both structural genomic information and functional genomic information of each genotype may be obtained.

As those of ordinary skill in the art will appreciate, there are a number of online bio-databases and analytical software being developed by governments, universities and private companies worldwide that can be used to retrieve the information in step 200. These databases give high-speed access to the information and tools similar to the well-known GenBank, Swiss-PROT and other DNA/protein databases. An example for agricultural genomic database is Agricultural Genome Information System maintained by USDA. This database contains genomic information for a number of crop plants. There are also plant genomic databases developed by a number of private organizations as well.

Handling of such massive databases of gene and protein sequence and structure/function information is known in the art. For example, Bioinformatics, which is the application of computer technology to the management of biological information, is being used to gather, store, classify, analyze and distribute biological information derived from sequencing and functional analysis projects around the globe. There are several different bioinformatics tools available over the Internet free of charge. For instance, at the European Bioinformatics Institute (Cambridge, UK) there are more than 500 of these tools. There are concerted efforts to make the tools of bioinformatics as standardized and easy as possible, similar to the aggressive development of standardized computer operating systems. Thus, in step 200, a genomic database can be accessed through a bioinformatics program that provides an infrastructure through which information on genetic variables for one or more cultivars to be used by the customer can be collected, catalogued and stored in a database.

In step 210, both agronomic and environmental factors (growth conditions) that influence a selected crop plant growth, yield and quality of the product are =obtained to develop a database containing site-specific farming data. Such data enables monitoring of crop health, identification of crop variability and allocation of resources such as fertilizer, lime, pesticides and fungicides. The agronomic and environmental factors that influence a number of crops around the globe are well known in the art. For example, it is well known in the art that cranberry yield is dependent upon a number of agronomic (horticultural) and environmental factors, all of which affect fruit set, berry enlargement and number flower per upright stalk. Further, it is known in the art that larger berries would result from increased bee activity. Cranberry products such as sauce, juice, frozen concentrate and consumer products have become very high in demand. This demand necessitated tremendous increase in the yield per acre of cranberry fruit by good farming practices, pest and disease control. It is well known that cranberries require a high water table, specific soil characteristics and pH, drainage and organic material that are basically a wetland soil classification. Cranberries require very little fertilizer compared to most upland crops such as corn, however, they do require some pesticides and fungicides. Thus, there is a good wealth of site-specific farming data because predicting yield is of great interest to growers in considering the value of the cranberry as a commodity.

To obtain the relevant information in step 210, one practicing this invention can take advantage of the recent improvements in the field of agriculture such as GPS technology data and GIS databases. These are well known in the art. For example, data from Global Positioning System (GPS) and various remote sensors are used to develop the Geographic Information Systems (GIS) database. The GIS is a computer-based tool for mapping and analyzing things that exist and events that happen on earth. GIS provides certain benefits in tabulating and visualizing data detected by GPS and other techniques such as remote sensing techniques such as imaging cameras. For example yields can be estimated while crops are still growing in the field. Satellite-based GPS devices enable the determination of precise locations within a field of interest. GIS enables data management of detected conditions on a field of interest. Both GPS technology and GIS are well known to those of skill in art. For example, one suitable GIS is presently available from Environmental System Research Institute, Redlands, Calif. Such a GIS system enables the management of agricultural information by ways of a graphical user interface that easily enables a user to tabulate data and evaluate collected data for making decisions about a crop being cultivated.

Further, these techniques provide a non-intrusive means of acquiring the agronomic and other related information from individual sites as well as on a regional scale to enable crop management decisions. GPS allows for the collection of insect, disease, yield and soil pH information at the field level while recording spatial locations of the observations. Factors important to growers such as soil type, pH, soil nutrients, soil nitrate levels, organic matter, insect location and counts presence or absence of fungal pathogens, weeds, soil compaction, and soil nutrients number and condition of flowers and fruits, upright density and canopy height can be measured for site specific management.

The GPS data can be coupled with other devices and imaging techniques for determining variables such as soil characteristics, yield goals, crop flowering and maturity, and infestation in an area being studied. Satellite imaging techniques (e.g. thermal imaging) and air-photos (in the visible, infrared and ultraviolet ranges) have enabled the collection of large amounts of data to characterize agronomic information and features on large fields of interest. These and other detection devises have enabled the collection of agronomic information while crops are being grown but without harming crops during the detection process, in order to make projection on crop-yield during a particular growing cycle. Further, recent advances in technology has lead to the development of new instruments that will allow access to a wide range of digital imagery from both aircraft and space borne platforms in the conversion of conventional imagery into digital format.

Such agronomic information is presently available or can be obtained in a database such as in a GIS database format. Output maps can be created from the GIS files indicating the spatial distribution and intensity of disease, insect outbreak, plant yield, and the specific nature of the relationship between variables such as soil pH, weed density, and crop yield. Thus, the information in step 210 includes in-site GPS crop data at the field level, air photos, land use/land cover, hydrology, wetlands, roads, elevation, slope, soil type, the proximity of the fields to the processing facility, transport methods, refrigeration etc., and can be used to develop site-specific GIS information. Such information can be useful in predicting overall crop yields and efficiency. Certain types of imaging techniques can be used to assess maturity and hence guide optimal timing of harvest. Further, in accordance with the present invention such information can be used to make further correlation with genetic, structural and functional, and processing variables to allow a grower to make reasoned decisions such as to continue to grow the selected crop in the area of interest or to genetically alter the crop based on the predictions of the current crop yield.

Along with the genomic and growth conditions information, the range of structural and functional features of a given product encoded by the genetic variables of a crop plant grown under different agronomic and environmental condition is also obtained by accessing the information in steps 200 and 210. All of this information is stored in step 240 in a database which is described in detail below with reference to FIG. 3.

Referring now to FIG. 3, there is shown a database with a plurality of records 250a, 251a . . . 252x. Each record contains a set of genomic data (genetic variables) information fields 253a, 254a . . . or 255x. Each set of genomic data information fields is representative of a particular cultivar (FIG. 3A cultivar 1, FIG. 3B cultivar 2 . . . or FIG. 3C cultivar X). Each record also contains a particular set of growth conditions information fields 240a, 241a . . . or 242x under which the particular cultivar is to be grown. In this respect, each set of genomic information field representing the particular cultivar (e.g., 253a) corresponds to the particular set of growth conditions information fields (e.g., 240a). In addition, each set of genomic data information fields 253a, 254a . . . or 255x corresponds to a given set of product feature range fields 256a, 257a . . . or 258x. Records 250a, 251a . . . 252x are constructed as discussed above using publicly available information. By using these records one practicing the invention can readily discern the product features that are expected of a given cultivar when grown under a given set of growth conditions prevailing in a particular geographic location.

In step 250, the indices from step 190 are compared to each set of product feature range fields 256a, 257a . . . or 258x. The set of product feature ranges that include within their limits or match the values of the indices from step 190 is then selected, and the set of genomic data information fields associated with this selected set of product feature ranges is then "correlated" with the indices stored in step 190. In this way, the indices from step 190 are used to identify a cultivar. Thus, after step 250, a particular cultivar has been associated (or correlated) with the sample from step 50.

The correlation identifies the cultivar as well as genotype of the cultivar associated with the indices stored in step 190 for the sample from step 50. The identified cultivar after the correlation should correspond to the cultivar information provided by the customer. For example, after the correlation of genomic data information fields with the indices stored in step 190 for tomato fruit, the tomato cultivar identified is 'Mountain Supreme', then the customer provided the information about the cultivar should also be 'Mountain Supreme'. If the name of the cultivar obtained from the customer happens to be different (e.g., "Olympic") then the customer provided name is disregarded and the customer is recommended to grow 'Mountain Supreme' at step 500. The steps that lead to recommendation for growing a given variety in step 500 are described elsewhere in this document.

It should be noted that, in one embodiment, before recommending that the customer grow a particular variety in a particular geographic location at step 500, the structural and functional variables in step 190 are correlated with agronomic and environmental variables in a location (See FIG. 3) where the sample 50 is to be grown or from where the sample 50 is collected. As already described above, correlation of structural and functional variables with genetic variables ensures that the identified variety has the particular genetic make-up that is required by the customer. However, the phenotypic value of a feature (e.g. high lycopene or low lycopene and the amount of lycopene, high protein or low protein, the amount of protein, fruit size etc.) includes both a genetic and an environmental component (where the product features of a given cultivar is impacted by different growth conditions), and a genotype-environment interaction (where the product features of different cultivars are impacted under the same set of growth conditions). Therefore, correlation of structural and functional variables with the agronomic and environmental variables associated with the variety of interest allows the present invention to assess how the product features of a given cultivar in step 190 may be impacted by agronomic and environmental variables associated and to optimize the agronomic and environmental variables for the given cultivar in a location chosen by the customer. The correlation also allows to determine how different genotypes respond under a given set of environmental conditions. The overall information enables the breeders or others to make higher probability of cross-matches in order to achieve desired parameters. The terms, environmental or growth conditions as used herein can also include agronomic variables even if not specifically stated.

It is well known that gene expression by plant cells is continuously modulated by local environmental cues. Biotic and abiotic stresses elicit their own programs of acute or chronic gene expression. For example, much has been learned about how plants sense their environment and how primary signals are transduced into growth responses (Bowler et. al., 1994, Plant Cell 6:1529–1541; Quail et. al., 1995, Science 268:675–680; Ecker, 1995, Science 268: 667–675. Similarly, biochemical mechanisms that permit plants to recognize pathogens and insect pests (biotic stresses) and then mount defensive responses have resulted in the introduction of agricultural chemicals to stimulate their defense systems. Also, for example, it is well known that ethylene is a key regulator of plant growth and development and its synthesis can be triggered by wounding (e.g., by pests) and environmental stresses, and the presence of the hormone can trigger the expression of various genes. Various processes are known to be affected by this hormone including fruit ripening in tomatoes.

Further, for example, certain crop plants selectively aid the growth of the specific types of beneficial microorganisms. Some microorganisms for instance have been shown to provide growth factors for plants and protect plants against insect attack and infection. Legumes such as soybeans rely on microorganisms living inside their roots to fix nitrogen for the plants' metabolic processes. A number of genes are known in the art that enhance the nitrogen-fixing process and the specificity of the microorganism for its host. There are not only interspecies differences in plants to act as hosts for beneficial (symbiotic) micro-organisms, there are also intervarietal differences. Therefore, the correlation of the information in steps 190 and with the data such as shown in FIG. 3 can aid in making decisions to improve the consistency of performance of selected crops.

Referring again to FIG. 3, there is shown a database with a plurality of records 250a, 251a, 252a for cultivar 1 (FIG. 3A) 250b, 251b, 252b for cultivar 2 (FIG. 3B) and 250x, 251x, 252x for cultivar x (FIG. 3C). Each record contains a first set (240a, 240b, 240x) a second set (241a, 241b or 241x) and a third set (242a, 242b or 242x) of growth conditions information fields. Each set (e.g., 240a, 241a, or 242a) of growth conditions information fields represents a set of agronomic and environmental variables prevailing during a particular growth stage (seedling stage, flowering stage, fruiting stage etc.) of a given cultivar (e.g., cultivar 1). In addition, each set (240a, 241a, 242a, 240b, 241b, 242b, 240x, 241x or 242x) of growth conditions Information fields corresponds to a given set of product feature range fields (256a, 257a, 258a, 256b, 257b, 258b, 256x, 257x, or 258x, respectively, developed from the already available information. The relationship between a given pair of sets (e.g. 240a, 256a) is such that when raw product (e.g. tomato fruit) that has indices (e.g., the indices stored in step 190) falling within or matching the limits of product feature range set (e.g., 256a), then a determination is made that the selected cultivar 1 should be grown under the growth conditions specified in the corresponding growth conditions information field set (e.g., 240a) in order to be able to produce the products that meet the required quality standard.

Once a particular product feature range set is identified, then the corresponding genomic information (and thereby the corresponding cultivar) and the corresponding growth conditions under which the particular cultivar can be grown to produce products having the expected structural and functional features. It should be noted that for comparison of indices with product feature range sets, either measured indices from step 190 or customer desired indices or values (which can also be stored in the database in step 190) are used. These customer desired indices or values can be compared to the databases as shown in FIG. 3 to identify the required growth conditions information and to identify the cultivar and its genotype as explained above. In this way, both cultivar and growth conditions can be identified by comparing the indices (in 190) with product feature range sets such as that illustrated in FIG. 3. And, the correlation of the data in 190 with the growth conditions and genomic information allows to produce products having the expected structural and functional features because by growing the identified cultivar (as already described above) under the identified growth conditions (e.g., 240a), it is possible to predict the product feature range (e.g., 256a).

If the customer chooses a different geographic location that has different set of grow conditions (e.g., growth conditions Set 2, 241a) to grow the cultivar 1, then the customer can be cautioned of the expected structural and functional features (e.g., product feature range set 2, 257a) before large scale production is undertaken by the customer.

In FIG. 3 it is shown that a product feature range of a particular cultivar is dependent on the growth conditions under which the particular cultivar is grown. The impact of each growth condition or variable (such as day temperature, photoperiod, soil fertility, soil moisture etc.) on the product feature range depends on the genotype of the cultivar. For example, a given cultivar can be temperature insensitive and/or photoperiod insensitive or moisture insensitive. For example, if the cultivar 1 is day temperature (15–30° C.) and moisture (20%–50%) insensitive, this cultivar can produce a product with the same product feature ranges 256a, as long as the soil fertility is maintained at the same level (e.g., 6000 kg Nitrotgen/ha) even though the cultivar 1 is grown in geographic locations with day temperatures ranging from 15° C. to 30° C. and soil moisture ranging from 20% to 50%. Therefore, after the identification of the cultivar, information as to whether the particular cultivar has been known to be insensitive to one or more growth conditions is also gathered from the publicly available databases. Such cultivars that are insensitive to one or more growth conditions are already available and are known to one skilled in the art. Accordingly, cultivars that are insensitive to one or more growth conditions are also contemplated.

The database illustrated in FIG. 3, can also be used to advise the customer whether or not a particular cultivar, for example cultivar 1, identified by comparing indices (190) which match product feature range Set 1, 256a, can be used to produce a product with indices (e.g., which match 258a) different from that in 190 by simply searching records for cultivar 1.

There may be situations where correlation of indices from 190 with genetic variables may identify more than one cultivar. For example, the feature analysis 100 of a tomato fruit (sample obtained in step 50) may result in the following indices 190: fruit size 59 mm±SE; β-carotene 10 ppm±SE; lycopene 100 ppm±SE; total fruit sugars 68%±SE. Referring again to FIG. 3, comparison of indices from 190 with product feature range sets can identify both cultivar 1 and cultivar 2 that can be grown under the same growth conditions because the indices from step 190 fall within the limits of more than one product feature range fields (see 256a and 256b in FIG. 3). In those situations the choice is left up to the customer who may choose a particular cultivar based on various other considerations such as cost, availability, etc., of seed stock for large scale production of the product.

It should also be noted that, in some embodiments, the product feature range sets and the corresponding genomic information is stored in one database. The same product feature range sets and the corresponding growth conditions information for the cultivars are stored, instead, in a separate database.

The database shown in FIG. 3 can also be used to advise a customer to choose a particular cultivar over another cultivar. For example, there may also be situations where a customer already aware of equal performance of cultivars 1 and 2 under a set of growth conditions (e.g., set 1 in FIG. 3) chooses to grow cultivar 2 under growth conditions set 3 and expects to produce fruits having a mean size of 95 mm. The customer chooses to grow cultivar 2 for valid reasons such as the cost of the seed. However, the analysis of the database shown in FIG. 3 reveals that cultivar 2 when grown under growth conditions set 3 produces fruits having feature range of only 20–30 mm. On the other hand, by growing the cultivar 1 under growth conditions set 3, the customer can expect fruits having a mean size of 95 mm. Thus, the customer can be advised to choose cultivar 1 over cultvar 2 in order to produce the desired product.

The different responses of cultivar 1 and cultivar 2 to growth conditions set 3 described in the paragraph above is due to genotype-environment interaction. The genotype-environment interaction, which is known in the art, results because individual genotypes differ in their responses to variations in soil fertility, soil moisture, temperature, day length, light intensity, humidity, plant pathogens, cultural practices or other biotic and abiotic factors. For example, it is known in the art that protein content of wheat depends strongly on factors such as soil, nitrogen, soil moisture, and temperature during the growing season. Some varieties (or genotypes) produce more protein than others under particular growing conditions.

Figure 4A:
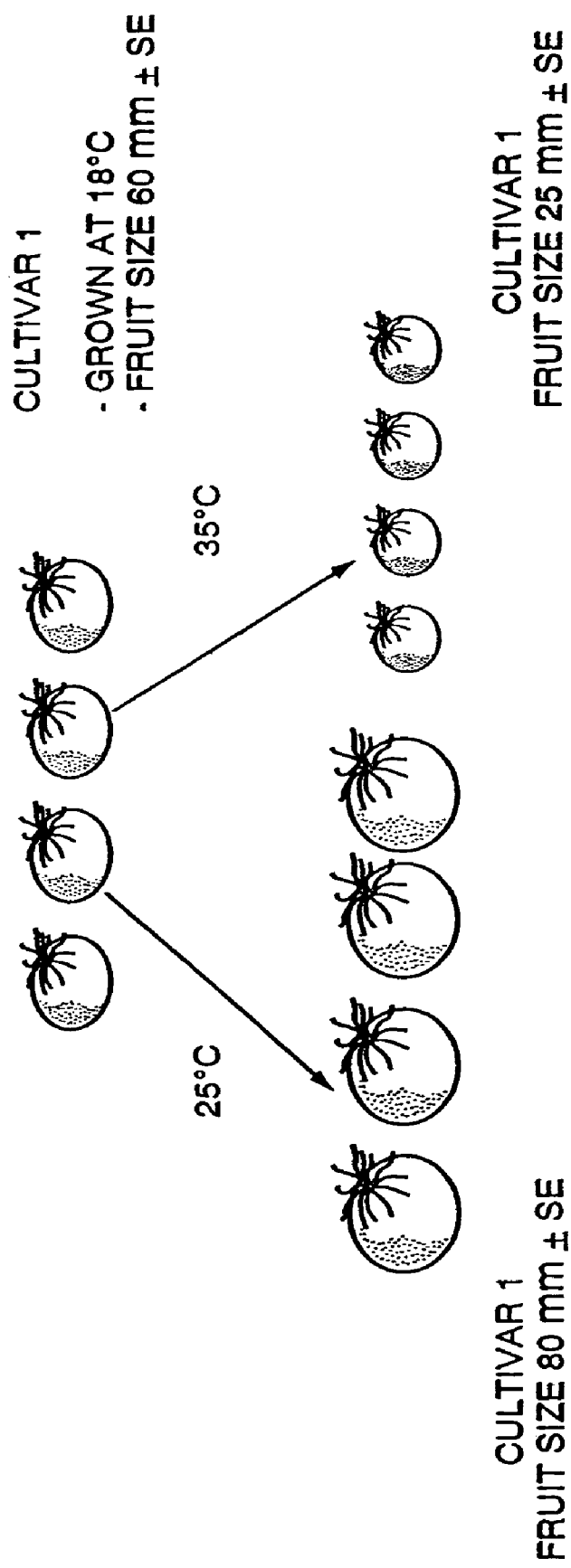
FIGS. 4A and 4B are illustrative examples of the influence of different growth condition on product feature values of a cultivar (FIG. 4A) and genotype-environment interaction of different cultivars (FIG. 4B).
Figure 4B:
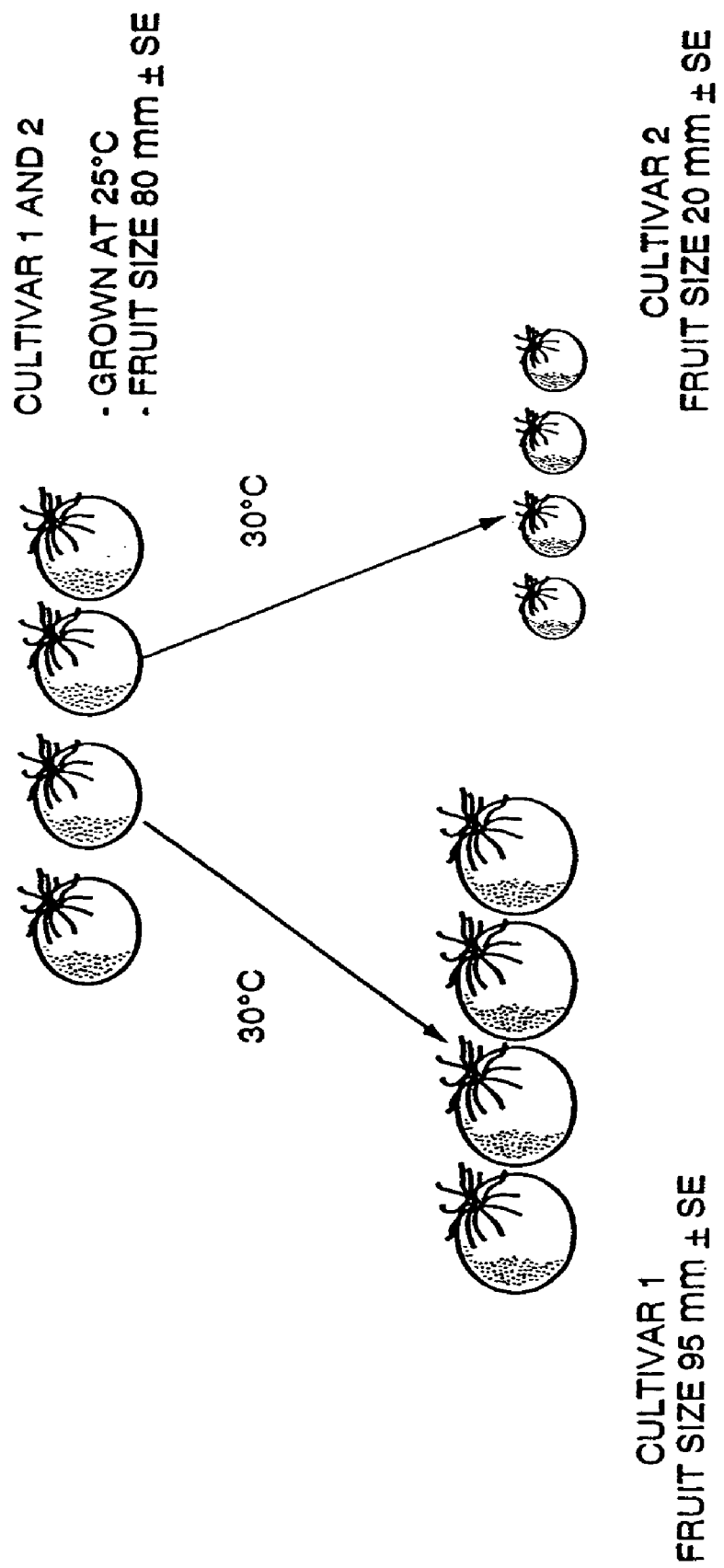

Illustrated in FIGS. 4A and 4B are simple examples of how the product features of a particular tomato cultivar is impacted by different growth conditions (FIG. 4A) and how the product features of different cultivars (FIG. 4B) are impacted under the same set of growth conditions. Referring to FIG. 4A, cultivar 1 yields fruits having a mean size of 60 mm when gown under a mean day temperature of 18° C., and a mean size of 80 mm when grown under a mean day temperature of 25° C. However, the same cultivar when grown under a mean day temperature of 35° C. produces fruits having a mean size of only 25 mm. Referring to FIG. 4B, both cultivar 1 and 2 produce fruits having a mean size of 80 mm when grown under a mean day temperature of 25° C. However, cultivar 1 produces fruits having a mean size of 95 mm when grown under a mean day temperature of 30° C. whereas cultivar 2 produces fruits having a mean size of only 20 mm when grown under a mean day temperature of 30° C.

The character designations such as $f_1$ $f_2$ $f_3$ $f_4$ for size gene(s), $hp_1$ $hp_2$ $hp_3$ $hp_4$ for lycopene content gene(s), fruit sugar gene(s) $s_1$ $s_2$ $s_3$ $s_4$ and β-carotene gene(s) $B_1$ $B_2$ $B_3$ $B_4$ in FIG. 3 are shown for purposes of illustration only. The character designations can be indicative of multiple genes for each trait, multiple alleles of a gene and/or the expression levels of a gene or genes for a particular trait (numeral 1 being the lowest expression level). Multiple alleles arise by repeated mutations of gene, each mutant giving different effects. An example of multiple genes responsible for wheat gluten levels is described below. For example, it is known in the art that there is qualitative (e.g., hp or og genes) and quantitative variation for lycopene in tomato. The gene(s) can be dominant or recessive. For example, it is also known in the art that the gene for β-carotene is a dominant gene.

Parameters required to process the raw material (e.g., tomatoes of a given variety in the illustrative example) to a final product (e.g., ketchup in the illustrative example) are provided in step 300. These can include sorting time, personnel for sorting, selection of treatments (such as steam peeling), identification of mold or pest infestations, selection criteria for the quality product and so on. For example, conventional processing of tomatoes to standard formatted products such as sauce, juice and paste includes generally of the following procedures: milling the tomato, finishing to remove skins and seeds, reducing the particle size of the pulp, evaporation and aseptic filing. Various modifications to the conventional processing have been made to improve the quality. For example, during conventional industrial processing of tomatoes it is well known that there is considerable loss of viscosity. This loss is reduced by heating the tomato before removal of skins and seeds, a process known in the industry as breaking. Further known modification of breaking is cold break which results in products that are of high quality in flavor and color. Here the milled tomatoes are heated only to temperatures of 70–75° C. (instead of 95–100° C.) to denature the enzyme polygalactouronase in tomatoes.

Figure 5:
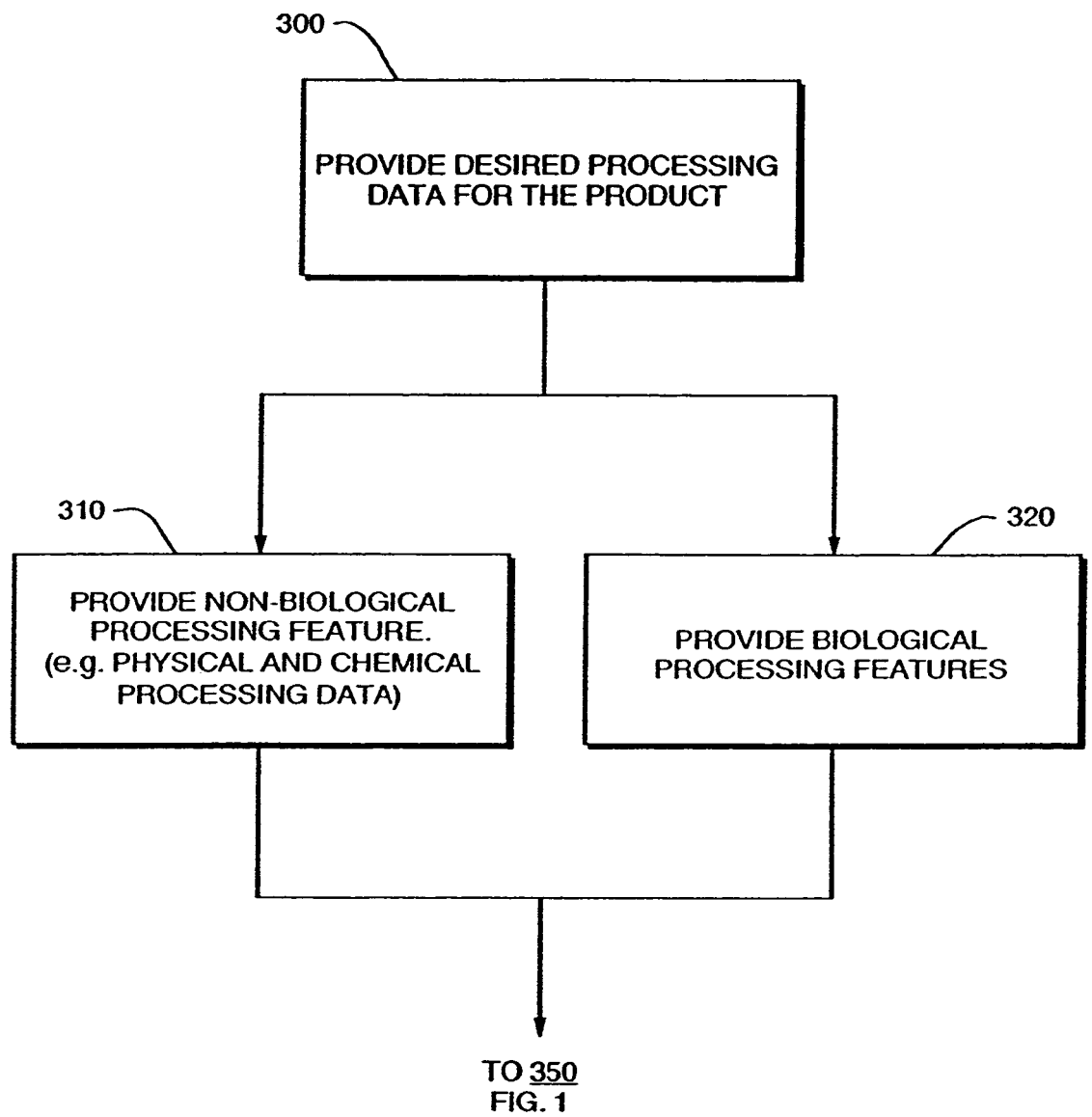
FIG. 5 is a flow diagram of a method for providing different processing parameters.

The processing parameters in step 300 include both non-biological (chemical, physical) processing features 310 and biological processing features 320 as shown in FIG. 5. It is known in the art that the demand for new and improved commercial products is being met through bioprocessing as well. Bioprocessing is carried out by living organisms or their cellular components (digestive enzymes). In fact, bioprocessing can offer a level of specificity, predictability and productivity that otherwise would not exist in the manufacture of certain products. A well known example of such a process is fermentation which converts glucose sugars derived from plant products into commodity chemicals using microbes cellulose, a polymer of glucose molecules, can be hydrolyzed to form glucose, which in turn can be bioconverted into a variety of products such as ethanol. It should be noted that periodic sampling during processing for analysis of post-processing microphenomics is often necessary and this data is provided at step 300 as well.

As discussed more fully below, the indices provided in step 190 are correlated to the processing parameters provided in step 300 to determine whether the customer supplied product fits into the desired processing parameters in step 350.

Referring now to FIG. 6, there is shown a database with a plurality of records 350a (FIG. 6A), 350b (FIG. 6B) . . .

350x (FIG. 6C). Each record contains a first set 352 of product processing data information fields, and a second set 354 of product feature range fields 354. Each set (352a, 352b . . . 352x) of product processing data information fields represents a set of processing parameters (e.g., specific mill time, specific heat time, specific heat temperature, amount of heat etc.) In addition, each set (352a, 352b . . . or 352x) of product processing data information fields corresponds to a given set of product feature range fields 354a, 354b . . . or 354x. For example, the amount of heat required to change the temperature of a material (e.g., tomato fruit) from $T_1$ to $T_2$ depends, among other things, on the mass of the material. Specific ranges of the mass of the material is provided in product feature range fields and the amount of heat is provided in product processing data fields. The relationship between a given pair of sets (e.g., 352a, 354a) is such that when raw product (e.g., tomatoes) having indices (e.g., the indices stored instep 190) falling within the limits of product feature range set 354a is subjected to processing using the parameters reflected by product processing data information field set 352a, the resulting output (e.g., ketchup) meets a predetermined uniform quality standard. In step 350, the indices (from step 190) are compared to each set of product feature range fields 354a, 354b . . . 354x to see if a set of product feature ranges exists that includes within its limits the values of the indices from step 190 in order to determine whether the customer supplied product fits into the desired processing parameters. In step 351 a query is made as to whether or not indices 190 match a record 350. If the answer is "yes", then the products from sample 50 can be processed to produce an acceptable final product (e.g., ketchup), and in step 500 a recommendation is made to grow the variety associated with sample 50.

For example, lycopene, the red pigment of the tomato is used as a natural coloring material for food products. This pigment is also an immediate precursor to β-carotene, the provitamin that is readily converted in human bodies to vitamin A. In the lycopene industry, high lycopene containing tomatoes are preferred as raw materials of the process. The higher the content of lycopene in the tomato, the greater the flexibility of the process and the ability to control the amounts of various materials which are produced at a given time. By correlating the microphenomic feature (i.e., the lycopene content of the pulp from tomatoes of the customer selected cultivar) to the processing requirements of lycopene industry, it is possible to make reasoned selections of tomato cultivars for the required lycopene content so that variations in lycopene content and hence the quality of the processed product can be avoided. For example, if one of the product feature ranges is 90–100 ppm (parts per million) of lycopene content in the pulp, then the tomatoes of a cultivar having less than 100 ppm lycopene do not fit into the desired processing feature or parameter. If the feature analysis for the lycopene content reveals that the customer provided tomatoes do contain lycopene content of 100 ppm, then the tomatoes from that cultivar or variety fits into the processing parameter and therefore the feature in 190 matches a record 350. Then that particular cultivar is recommended for growing at step 500. Additionally, the method of the present invention allows the evaluation of variants for lycopene content genes or related genes so that variant cross-matches can be proactively made to enhance this variable.

Alternatively, if the recommendation for growing the cultivar or variety cannot be made after step 351, (e.g., if the answer to the query at 351 is "no" then further query is made in step 352 i.e., whether [x] is greater than threshold 1 or whether [y] is greater than threshold 2, where x is Euclidean distance between indices (from step 190) and closest Product Feature Range Set (e.g., 2564a, 256b or 256x) and where y is the maximum over all indices of the quality [Indice 190—corresponding feature from closest Product Feature Range Set]. In other words, in step 352 a calculation is made to see whether the difference between values for all of the indices from step 190 and product feature range set (e.g., 257a, 257b or 257x) for each cultivar is greater than threshold 1. Similarly, a calculation is made to see whether the difference between the value for each index from step 190 and the corresponding feature from product feature range set is for each cultivar is greater than threshold 2. Further steps in the method depends on the answer to the above query. See FIG. 1. The particular values at which threshold 1 and threshold 2 are set are a matter of design choice and, as explained below, represent the difference between recommending that a genetic modification be made to the existing cultivar or, in the alternative, recommending that a totally new cultivar be grown.

Thus, if the products from sample 50 cannot be processed to produce an acceptable final product (for example, uniform quality ketchup) then a determination is made that the product of the given cultivar obtained in step 50 is not suitable for processing into the acceptable product. In such a case, one of the two following strategies can be followed depending on the extent of modification required to produce the desired cultivar.

In the first strategy, a genetic and molecular manipulation approach is explored to produce the desired cultivar depending on the ease with which the genes for the missing traits can be moved into and expressed in an elite genotype or cultivar already selected by the customer in economically viable time frames. For example, assume that the values of the indices for tomato fruit such as for size and total sugar content determined in step 190 fall within the product feature range of set 1, 256a, referred to in FIG. 3. However, it was found in step 351 that indices 190 do not match a record 350 and, therefore, that the tomatoes from the given cultivar is not suitable for processing into the acceptable final product because, for example, β-carotene content is less than 1 ppm or lycopene content is less than 55 ppm. In such a case, a gene for β-carotene or lycopene can be introduced into the elite genotype of the cultivar already selected by the customer which cultivar is desirable in all respects but for low levels of β-carotene or lycopene content in the fruit. The expression patterns of the introduced gene can also be controlled. For example, the gene for β-carotene synthesis can be placed under the control of tomato fruit-specific promoters so that the provitamin A (β-carotene) can be produced only in the ripening fruit. Thus, when this strategy is to be followed one can look for β-carotene gene, for example, in a tomato genomic database or other genomic databases in step 700 to determine whether the gene for β-carotene is available in any of the genomic databases. If available, then a suitable genetic engineering and molecular manipulation approach is recommended in step 800. The genetically engineered cultivar may now have the values of the indices for tomato fruit that match a record 350. Steps 700 and 800 are described further in the paragraphs below.

A second strategy, i.e., a search for variety with a suitable genetic background, is followed if the above mentioned first strategy is not adopted. The information stored in step 240 for the crop in question is accessed at step 600 to see whether a variety with a suitable genetic background is available. Referring to the tomato example above, for example, there can be a situation where several values of the indices for tomato fruit such as for size, β-carotene and lycopene contents, in step 190 fall below the product feature range set 1 in 256*a*. In such a case genetic engineering and molecular manipulation approach can be complex, and can even result in a tomato cultivar undesirable in certain other respects. A search for a variety with a suitable genetic background can be economically more viable than genetic engineering for several traits. Further, it is also possible that a customer is unwilling to adopt genetic engineering approach for various reasons. Accordingly, in step 600, for example, the tomato crop information stored in step 240 database can be accessed to see whether a variety with a suitable genetic background or genotype is available. A search for a genotype that can produce the selected product with the values of the product features that have the closest match to a record 350 having a set of product processing features. Although the product feature values (e.g., 256X in FIG. 3) of the selected genotype after step 600 do not fit exactly into one of the product processing feature range sets (e.g., 354*b* in FIG. 6), it should still be possible to predict the quality of the end product after subjecting the raw product to the corresponding product processing parameters (e.g., 352*b* in FIG. 6). Specifically, the end product may be of different but uniform availability depending on whether the product features of selected genotype have the values that fit into the product processing feature range set or have values that closely match the product processing feature set; The end product in the former case is of first grade quality while that in the latter case is if second grade quality. Preferably, the values of the product features should have the closest match to a record 350 such that [x] is less than threshold 1 or [y] is less than threshold 2. Thus, a suitable genotype is selected after the search in step 600. Product (e.g., tomato fruit) from the selected variety is obtained in step 50 and is subjected to necessary method steps so as to make recommendations in step 500. The analysis is to ensure that the variety recommended in step 500 does in fact yield products that meet the required product features for processing as described above before large scale production of the crop is undertaken by the customer.

In some embodiments a search for a variety with a suitable genetic background in step 600 can be combined with genetic engineering approach after step 700 for further refinement of the processing features.

Figure 7:
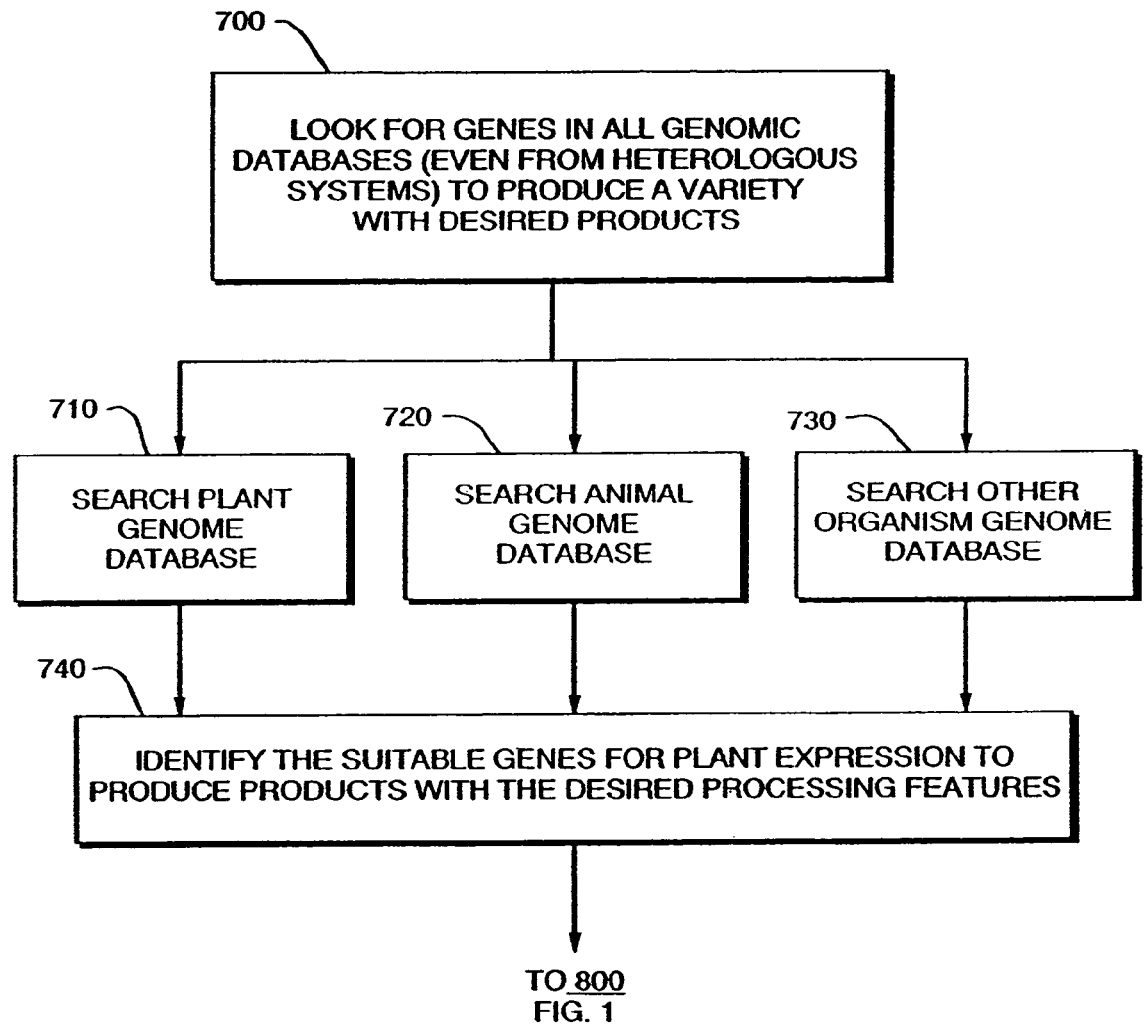
FIG. 7 is a flow diagram of a method for searching all genome databases.

As described above, the genetic and molecular manipulation approach is explored as one of the strategies to produce the desired cultivar that yields products suitable for processing into the acceptable product. First, a search for genes controlling the desired structural and functional features is made in step 700. As shown in FIG. 7, the search for suitable genes can be made in databases such as plant genome databases 710 (other than that for the selected crop), animal genome databases 720 or other organism genome databases 730. Once the genes for plant expression to produce products with the desired processing features, step 740, then a suitable genetic and molecular manipulation approach or the highest probability of cross-matching approach is recommended to the customer to produce the desired variety, step 800.

Other organism genome databases 730 can be those that are not covered under plant genome databases 710 or animal genome databases 720 that are currently available. For example, *C. elegans, Mycobacterium*, screwworm databases are classified separately in the genome database maintained by the United States Department of Agriculture (USDA).

It is well known that crop plants can be genetically engineered by using genes from the same or different species. For example, genetic engineering can be used to qualitatively change the composition and functional properties of wheat grains. It is known that wheat gluten is a complex mixture of over 50 individual proteins (Tatham et. al., 1990, In Advances in Cereal Science and Technology, Vol. 10, Pomeranz (ed.), AACC, St. Paul, Minn.). The high molecular weight (HMW) subunits of wheat gluten are major determinants of the elastic properties of gluten that allow the use of wheat doughs to make bread, cakes, pasta, and a range of other foods. There are both quantitative and qualitative effects of HMW subunits on the quality of the grain, the former being related to differences in the number of expressed HMW subunit genes. Although all cultivars of bread wheat have six HMW subunit genes, due to gene silencing only few of these subunits are expressed. Each subunit accounts for about 2% of the total grain protein (Halford et. al., 1992, Theoretical and Applied Genetics, 83:373–378). Therefore, the variation in gene expression within a cultivar or among cultivars can result in differences in the total amount of HMW subunit protein and hence the amount of elastic HMW polymers. Presence of a single HMW subunit in a cultivar can account for the higher quality as compared with a null or silent allele in a cultivar (Payne, 1987, Annual Review of Plant Physiology 38:141–153). Thus, in step 800, a customer desiring to produce wheat crop with 2%, 4%, 6%, 8%, 10% or a maximum ceiling of 12% of the total flour proteins can be recommended to manipulate the selected wheat cultivar for HMW subunit transgene expression. Alternatively, for example, wheat cultivars with only a null or silent allele for wheat gulten can be transformed with one, two, three, four, five and six alleles to obtain cultivars that show stepwise increases in dough elasticity and functional properties of the flour. Importantly, the method and information system provided herein enable one practicing the invention to more rapidly achieve the same parameters in the absence of genetic and molecular manipulation by higher probability of cross-matching.

It is also well known in the art that crop plants can be genetically engineered to produce products with desired qualities by using genes from other species, genera or heterologous sources. In fact, it is now virtually routine to incorporate stably almost any gene or set of genes into the crop of interest. For example, one desiring to produce sweet tasting tomatoes or lettuce can look for sweet protein encoding genes. *Dioscoreophyllum cumminsii* is a known source for sweet protein gene called Monellin. This sweet protein is 3000 times sweeter than sucrose. In fact, the transgenic expression of this gene in tomato has already been reported. (See Penarrubia et. al., 1992, Bio/Technology 10:561–564.) Thus, there are a number of reports known in the art demonstrating the capability to use transgenic expression of genes from heterologous systems (i.e., other than from the same species) to exquisitely design traits into agricultural products.

It is also well known in the art that once the gene from whatever source is introduced into the desired crop plant, the gene can be controlled through a number of gene promoters that have been identified for controlling expression patterns of introduced genes in sophisticated ways. Information about agromically important genes and genetic and molecular manipulations can be obtained from a number of private and public sources. For example, AGRICOLA database is one such source.

Due to the advent of novel biotechnological systems, the concern by the growers and the public in general that genetically engineered plants containing antibiotic and/or herbicide resistance genes may have dire consequences to environment and human health can now be obviated. Novel methods are now available to produce transgenic plants without the use of antibiotic resistance genes thereby avoiding the fears associated with the use of transgenic food crops and their products. For example, Kunkel et. al. (1999) report an antibiotic-free marker system to produce transgenic crop plants such as lettuce (see Nature Biotechnology 17:916–919). Similarly, Ebinuma et. al., (1997) report a "hit and run" selectable marker system which is also another antibiotic-free marker system (See Proc. Natl. Acad. Sci. USA 94: 2117–2121). Thus the ability to eliminate the antibiotic marker genes should reduce the possibility of adverse environmental impact from transgenic plants, while increasing their vigor, and the acceptability of transgenic plants by the public leery of genetically engineered food products.

Figure 8:
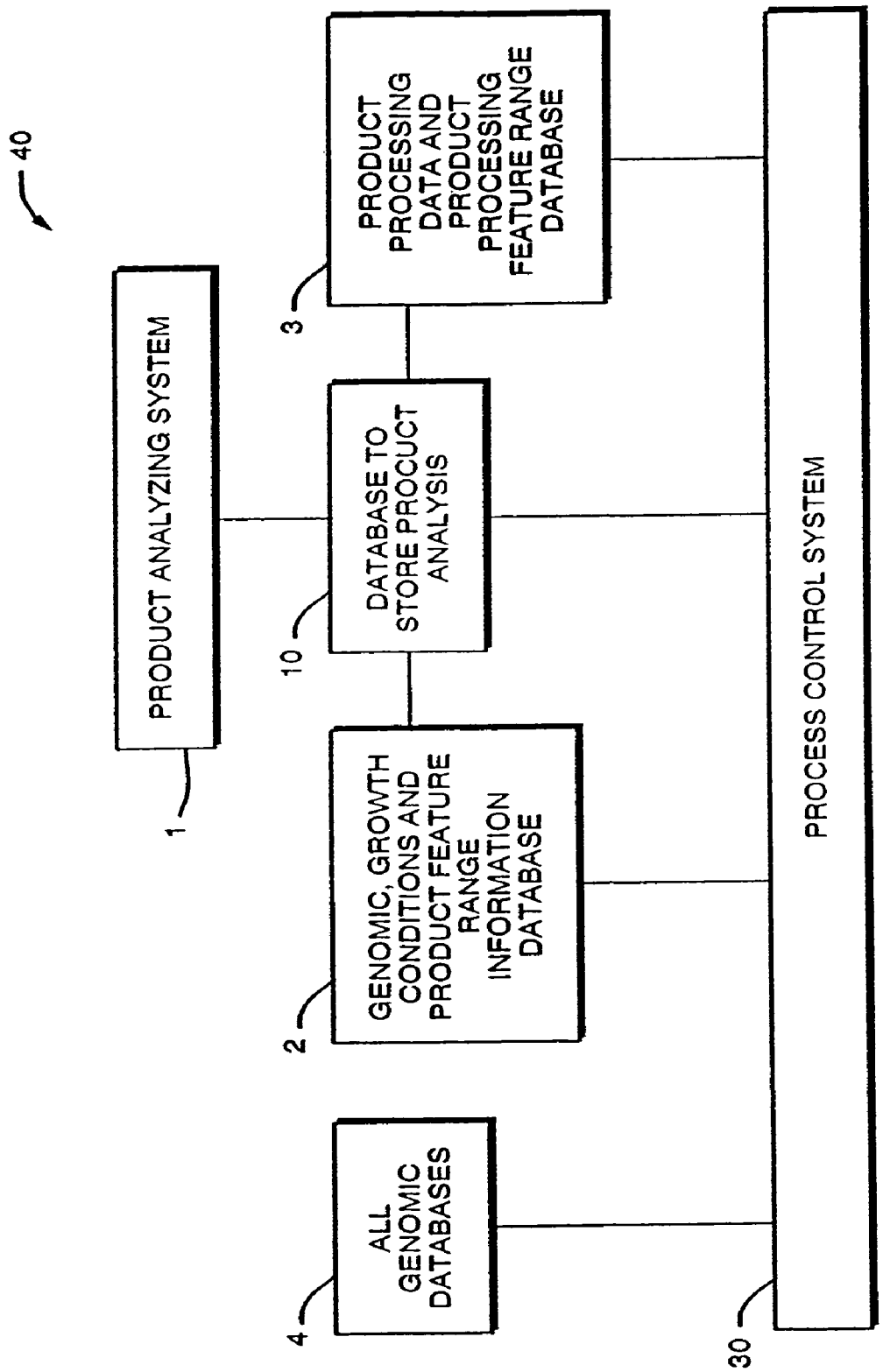
FIG. 8 is a schematic representation of the information system according to the present invention.

Referring to FIG. 8, an information system generally designated by reference numeral 40 is shown. Product analyzing system 1 can be used to determine the structural and functional features of a selected crop plant product or any living tissue. The structural and functional features include both microscopic structures including indices of the cell and intercellular level, and macroscopic structures each of which in turn include quantitative and quantitative traits. These features have already been exemplified in the paragraphs above. The product analysis is stored in the information system in a database 10 dedicated for this purpose. The product analyzing system is linked to the database memory so that the data can be stored in the database 10 as the analysis is completed for each structural and functional feature. The information system has a database memory for storing genomic and environmental information 2. This database memory can include genetic variable of the selected crop plant product or any living tissue and optionally the genetic variables for the selected crop plant itself. The genetic variables specific to each cultivar is maintained in one field, separate from the genetic variables specific to another cultivar. In addition, the database memory 2 can include agronomic and environmental conditions, and range of structural and functional features of a product (product feature ranges) encoded by the genetic variables of a selected crop plant under different agronomic and environmental conditions under which the selected crop plant is grown and/or to be grown. In an alternative embodiment, there can be one database memory to store the genetic variables and the corresponding product feature ranges of a cultivar and another database memory for different growth conditions under which the selected cultivar is grown and/or to be grown and the corresponding product feature ranges of the same cultivar. The information system further includes a database memory 3 for storing processing features of the selected products. The database 10 containing the structural and functional variables is in communication with the databases 2 and 3 (to form relational database) to perform correlation analysis among these variables. Particularly, the correlation analysis among these variables are performed so as to facilitate the non-random selection of the desired crop cultivar to be grown in a selected location under the given environmental conditions to produce products with desired processing features.

The information system 1 further includes a process control system 30. The process control system can be linked to publicly available all genomic database to identify and select specific genetic variables. Preferably, the process control system is used to identify and select specific genetic variables from one or more classes of databases so as to produce a product having product feature values that fall within one or more of the product processing feature ranges stored in the database or to produce a product having product feature values that closely match one or more of the product processing feature ranges. For example, the process control system 30 can be used to identify the specific generic variables that are missing in the database 2 so that the missing genetic variables can be identified from sources in all genomic database 4. The customer can be provided with this information and can be recommended to use genetic molecular manipulation approach. Alternatively the process control system 30 can be used to identify a cultivar having the genetic variable that encode product features whose values closely match to those of the Product processing features stored in database 3. Thus, the process control system 30 can be used to identify the needed plant (hybrid or natural genomes or transgenic) genomes that can be created by genetic and molecular manipulations. All of the databases (i.e., databases 10, 2, 3 and 4) described above can be linked to the process control system 30 to create a multi-dimensional information matrix.

The availability of this data in a comprehensive database can lead to the precision in the optimization of plant product consistency reaching processing industries, to the selection of seeds for growth to obtain products having consistency and to the ability to develop new designer seeds according to the needs of the processing industries around the world.

Reasoned selections of the crop members of the families identified in the paragraph below are particularly contemplated. The plant members used in the present methods also include interspecific and/or intergeneric hybrids, mutagenized and/or genetically engineered plants. Those skilled in the art understand the different types of plants. The term "crop member" refers specifically to species which are commercially grown as sources for fruits, vegetables, grains, nuts, forage, fodder fiber, flowers, condiments and oilseeds.

These families include and not limited to Leguminosae (Fabaceae) including pea, alfalfa, and soybean; Gramineae (Poaceae) including rice, corn, wheat; Solanaceae particularly of the genus *Lycopersicon*, particularly the species *esculentum* (tomato), the genus *Solanum*, particularly the species *tuberosum* (potato) and *melongena* (eggplant), the genus *Capsicum*, particularly the species *annum* (pepper), tobacco, and the like; Umbelliferae, particularly of the genera *Daucus*, particularly the species *carota* (carrot) and *Apium*, particularly the species *graveolens dulce*, (celery) and the like; Rutaceae, particularly of the genera *Citrus* (oranges) and the like; Compositae, particularly the genus *Lactuca*, and the species *sativa* (lettuce), and the like and the Family Cruciferae, particularly of the genera *Brassica* and *Sinapis*. Examples of "vegetative" crop members of the family Brassicaceae include, but are not limited to, digenomic tetraploids such as *Brassica juncea* (L.) Czern. (mustard), *B. carinata* Braun (ethopian mustard), and monogenomic diploids such as *B. oleracea* (L.) (cole crops), *B. nigra* (L.) Koch (black mustard), *B. campestris* (L.) (turnip rape) and *Raphanus sativus* (L.) (radish). Examples of "oil-seed" crop members of the family Brassicaceae include, but are not limited to, *B. napus* (L.) (rapeseed), *B. campestris* (L.), *B. juncea* (L.) Czern. and *B. tournifortii* and *Sinapis alba* (L.) (white mustard). While the products of crop plants are used as examples in the preceding paragraphs, the present invention can also be used to non randomly select uniform structural and functional features of products from wild plants so as to produce uniform quality end products.

All publications and references, including but not limited to patent applications, cited in this specification, are herein incorporated by reference in their entirety as if each individual publication or reference were specifically and individually indicated to be incorporated by reference herein as being fully set forth.

While this invention has been described with a reference to specific embodiments, it will be obvious to those of ordinary skill in the art that variations in these methods and compositions may be used and that it is intended that the invention may be practiced otherwise than as specifically described herein. Accordingly, this invention includes all modifications encompassed within the spirit and scope of the invention as defined by the claims.

What is claimed is:

1. A method for non-random selection of a raw plant product of a plant for processing into a uniform quality end product comprising the steps of:
   (a) obtaining one or more samples of the raw plant product from a customer;
   (b) analyzing the one or more samples to determine at least one structural or functional index associated with the raw plant product by means of an imaging system that is selected from one or more of the group consisting of a light microscope, fluorescent microscope, spectral microscope, hyper-spectral microscope, electron microscope, confocal microscope, optical coherence tomograph, spectral telescope, x-ray spectrometry, microtomy, nuclear magnetic resonance (NMR), inductively coupled plasma (ICP), ICP-mass spectrometry, scanning fluorimetry, magnetic resonance imaging (MRI), and ultrasound;
   (c) providing a plurality of product processing records, wherein each of the records associates a given set of product processing data with a corresponding product processing feature range set representative of the selected raw plant product, and wherein, for each such record, the uniform quality end product results from the manufacture of the raw plant product with the application of the given set of product processing data to raw plant product falling within the associated product processing feature range set;
   (d) determining the suitability of the one or more samples obtained in step (a) for processing into the uniform quality end product by comparing the at least one structural or functional index to the product processing feature range sets in the records; and
   (e) if the at least one structural or functional index matches one of the product processing feature range sets in the records then, selecting the raw plant product so that when processed under the given set of product processing data, the selected raw plant product results in the uniform quality end product.

2. The method of claim 1, wherein the selected raw plant product is a group of fruits, a group of tubers, a group of seeds, a group of leaves, a group of vegetative buds, a group of inflorescences, a group of nuts, a group of plant embryos, or a group of living tissue specimens having common characteristics.

3. The method of claim 1, wherein the at least one structural or functional index is a plant macrophenomics index or a plant microphenomics index.

4. The method of claim 1, wherein the at least one structural or functional index includes a qualitative feature.

5. The method of claim 1, wherein the at least one structural or functional index includes a quantitative feature.

6. The method of claim 1, wherein said processing data include bioprocessing data.

7. The method of claim 1, wherein said processing data is non-biological.

8. The method of claim 1, wherein said processing data is specific mill time, specific heat time, specific heat temperature, or amount of heat.

* * * * *